(12) United States Patent
Billot et al.

(10) Patent No.: US 10,160,739 B2
(45) Date of Patent: Dec. 25, 2018

(54) CRYSTALLINE FORMS OF DIMETHOXY DOCETAXEL AND METHODS FOR PREPARING THE SAME

(71) Applicant: Aventis Pharma S.A., Antony (FR)

(72) Inventors: Pascal Billot, Montreuil (FR); Marielle Dufraigne, Brunoy (FR); Hagit Elmaleh, Ormesson sur Marne (FR); Fabrice Mangin, Paris (FR); Patricia Rortais, Bourg la Reine (FR); Lionel Zaske, Saint Maurice (FR); Alexandre Giuliani, Boissy Saint Leger (FR)

(73) Assignee: AVENTIS PHARMA S.A., Antony (FR)

( * ) Notice: Subject to any disclaimer, the term of this patent is extended or adjusted under 35 U.S.C. 154(b) by 0 days.

(21) Appl. No.: 15/646,375

(22) Filed: Jul. 11, 2017

(65) Prior Publication Data

US 2018/0002302 A1 Jan. 4, 2018

Related U.S. Application Data

(60) Division of application No. 14/453,087, filed on Aug. 6, 2014, which is a division of application No. 13/767,966, filed on Feb. 15, 2013, now Pat. No. 8,846,959, which is a division of application No. 12/837,559, filed on Jul. 16, 2010, now Pat. No. 8,378,128, which is a continuation of application No. PCT/FR2009/000042, filed on Jan. 15, 2009.

(30) Foreign Application Priority Data

Jan. 17, 2008 (FR) .................................... 08 00243

(51) Int. Cl.
*C07D 305/14* (2006.01)
(52) U.S. Cl.
CPC .................................. *C07D 305/14* (2013.01)
(58) Field of Classification Search
CPC .................................................... C07D 305/14
See application file for complete search history.

(56) References Cited

U.S. PATENT DOCUMENTS

| | | | |
|---|---|---|---|
| 5,847,170 A | 12/1998 | Bouchard et al. | |
| 6,346,543 B1 | 2/2002 | Bissery et al. | |
| 7,241,907 B2 | 7/2007 | Didier et al. | |
| 8,575,373 B2 | 11/2013 | Henschke et al. | |
| 8,735,611 B2 | 5/2014 | Henschke et al. | |
| 8,901,322 B2 | 12/2014 | Lahiri et al. | |
| 2013/0065955 A1 | 3/2013 | Henschke et al. | |
| 2013/0211109 A1 | 8/2013 | Lahiri et al. | |
| 2014/0343133 A1 | 11/2014 | Didier et al. | |

FOREIGN PATENT DOCUMENTS

| WO | 9630355 A1 | 10/1996 |
|---|---|---|
| WO | 2005028462 A1 | 3/2005 |
| WO | 2011051894 A1 | 5/2011 |
| WO | 2013080217 A2 | 6/2013 |

OTHER PUBLICATIONS

U.S. Appl. No. 61/533,111, filed Sep. 9, 2011, Henschke; Julian Paul et al.
Brittain., et al., "Polymorphism in Pharmaceutical Solids," 1999, pp. 235-238.
Bryn., et al., "Solid-Stale Chemistry of Drugs," 2nd edition, 1999, SSCI, Inc. pp. 232-247.
Caira M.R., "Crystalline Polymorphism of Organic Compounds," Topics in Current Chemistry, 1999, vol. 198, pp. 163-208.
Chawla, et al., "Challenges in polymorphism of Pharmaceuticals," CRIPS, vol. 5, No. 1, Jan.-Mar. 2004, pp. 9-12.
International Search Report for Application No. PCT/FR2009/000042, WO2009/115655 dated Sep. 24, 2009.
Non-Final Office Action dated Apr. 14, 2015 for U.S. Appl. No. 14/301,740, filed Jun. 11, 2014.
Remington's Pharmaceutical Sciences; 17th edition 1987, Editorial Medica Panamericana—chapter VIII Preparados farmaceutims y su elaboracion, pp. 1912-1920.
Restriction Requirement as dated Dec. 8, 2011 for U.S. Appl. No. 12/837,559, filed Jul. 16, 2010.
Restriction Requirement dated Nov. 4, 2013 for U.S. Appl. No. 13/767,966, filed Feb. 15, 2013.
Rodriguez-Spong B., et al., "General Principles of Pharmaceutical Solid Polymorphism: A Supramolecular Perspective," Advanced Drug Delivery Reviews, 2004, vol. 56 (3), pp. 241-274.
Squillac., et al., Characterization of Delivery Systems, Differential Scanning Calorimetry, Encyclopedia of Controlled Drug Delivery., 1999, John Wiley 8 Sons, pp. 212-227.

*Primary Examiner* — Rebecca L Anderson
*Assistant Examiner* — Karen Cheng
(74) *Attorney, Agent, or Firm* — Kelly L. Bender

(57) ABSTRACT

The invention relates to anhydrides, solvates and ethanol hetero-solvates and hydrates of dimethoxy docetaxel or (2R,3S)-3-tert-butoxycarbonylamino-2-hydroxy-3-phenyl-propionate of 4-acetoxy-2α-benzoyloxy-5β,20-epoxy-1-hydroxy-7β,10β-dimethoxy-9-oxo-tax-11-ene-13α-yle, and to the preparation thereof.

1 Claim, 5 Drawing Sheets

CRYSTALLINE FORMS OF DIMETHOXY DOCETAXEL AND METHODS FOR PREPARING THE SAME

This application is a divisional of U.S. patent application Ser. No. 14/453,087, filed Aug. 6, 2014, which is a divisional of U.S. patent application Ser. No. 13/767,966, filed Feb. 15, 2013, now U.S. Pat. No. 8,846,959, which is a divisional application of U.S. patent application Ser. No. 12/837,559, filed Jul. 16, 2010, now U.S. Pat. No. 8,378,128, which is a continuation of International Patent Application PCT/FR2009/000042 filed Jan. 15, 2009, all of which are incorporated herein by reference; and which claim priority to French Patent Application No. 0800243 filed on Jan. 17, 2008.

The present invention relates to crystalline forms of dimethoxy docetaxel or 4-acetoxy-2α-benzoyloxy-5β,20-epoxy-1-hydroxy-7β, 10β-dimethoxy-9-oxotax-11-en-13α-yl (2R,3S)-3-tert-butoxycarbonylamino-2-hydroxy-3-phenylpropionate and to methods for the preparation thereof.

BACKGROUND OF THE INVENTION

4-Acetoxy-2α-benzoyloxy-5β,20-epoxy-1-hydroxy-7β, 10β-dimethoxy-9-oxotax-11-en-13α-yl (2R,3S)-3-tert-butoxy carb onyl amino-2-hydroxy-3-phenylpropionate exhibits notable anticancer and antileukaemic properties.

4-Acetoxy-2α-benzoyloxy-5β,20-epoxy-1-hydroxy-7β, 10β-dimethoxy-9-oxotax-11-en-13α-yl (2R,3S)-3-tert-butoxycarbonylamino-2-hydroxy-3-phenylpropionate is prepared according to the method which is described more particularly in PCT International Application WO96/30355 or PCT International Application WO99/25704. According to the method described in these applications, the product is not crystallized and is not characterized.

It was found that the acetone solvate of 4-acetoxy-2α-benzoyloxy-5β,20-epoxy-1-hydroxy-7β, 10β-dimethoxy-9-oxotax-11-en-13α-yl (2R,3S)-3-tert-butoxycarbonylamino-2-hydroxy-3-phenylpropionate (called form A) was completely determined and characterized according to the patent published under number WO2005/028462.

BRIEF SUMMARY OF THE INVENTION

The present invention relates to new crystalline forms, with the exclusion of the acetonate form, the only one known to date.

According to the present invention, it has now been found that certain anhydrous forms, certain ethanolic solvates or heterosolvates and hydrated forms have been completely characterized from a physical and chemical structure point of view.

DETAILED DESCRIPTION OF THE INVENTION

According to the invention, among the anhydrous forms of 4-acetoxy-2α-benzoyloxy-5β,20-epoxy-1-hydroxy-7β, 10β-dimethoxy-9-oxotax-11-en-13α-yl(2R,3S)-3-tert-butoxycarbonylamino-2-hydroxy-3-phenylpropionate, five different forms have been identified, among the ethanolic solvates or heterosolvates of 4-acetoxy-2α-benzoyloxy-5β, 20-epoxy-1-hydroxy-7β,10β-dimethoxy-9-oxotax-11-en-13α-yl(2R,3S)-3-tert-butoxycarbonylamino-2-hydroxy-3-phenylpropionate, four different forms have been identified and among the hydrates of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate, two different forms have been identified.

The five anhydrous forms identified were obtained according to the following methods:

The anhydrous form B by a method which consists in heating the acetone form or form A obtained according to the patent mentioned above, between 100 and 110° C. under vacuum or nitrogen sweeping. This treatment is preferably carried out for at least 9 hours before a return to ambient temperature without inducing chemical decomposition. Its melting point by DSC is approximately 150° C. The PXRD diagram of the anhydrous form B exhibits characteristic lines located at 7.3, 8.1, 9.8, 10.4, 11.1, 12.7, 13.1, 14.3, 15.4 and 15.9±0.2 degrees 2-theta.

The anhydrous form C is obtained by maturation of the acetone solvate form A, or of the anhydrous form B, in water followed by drying at up to 50° C. and maintaining between 0 and 5% RH at ambient temperature. Its melting point by DSC is approximately 146° C. The PXRD diagram of the anhydrous form C exhibits characteristic lines located at 4.3, 6.8, 7.4, 8.7, 10.1, 11.1, 11.9, 12.3, 12.6 and 13.1±0.2 degrees 2-theta. It is, among the various anhydrous forms, the least stable of all the forms described in the present invention. In the presence of a relative humidity of greater than 5%, it changes to a hydrated form.

Figure 1:
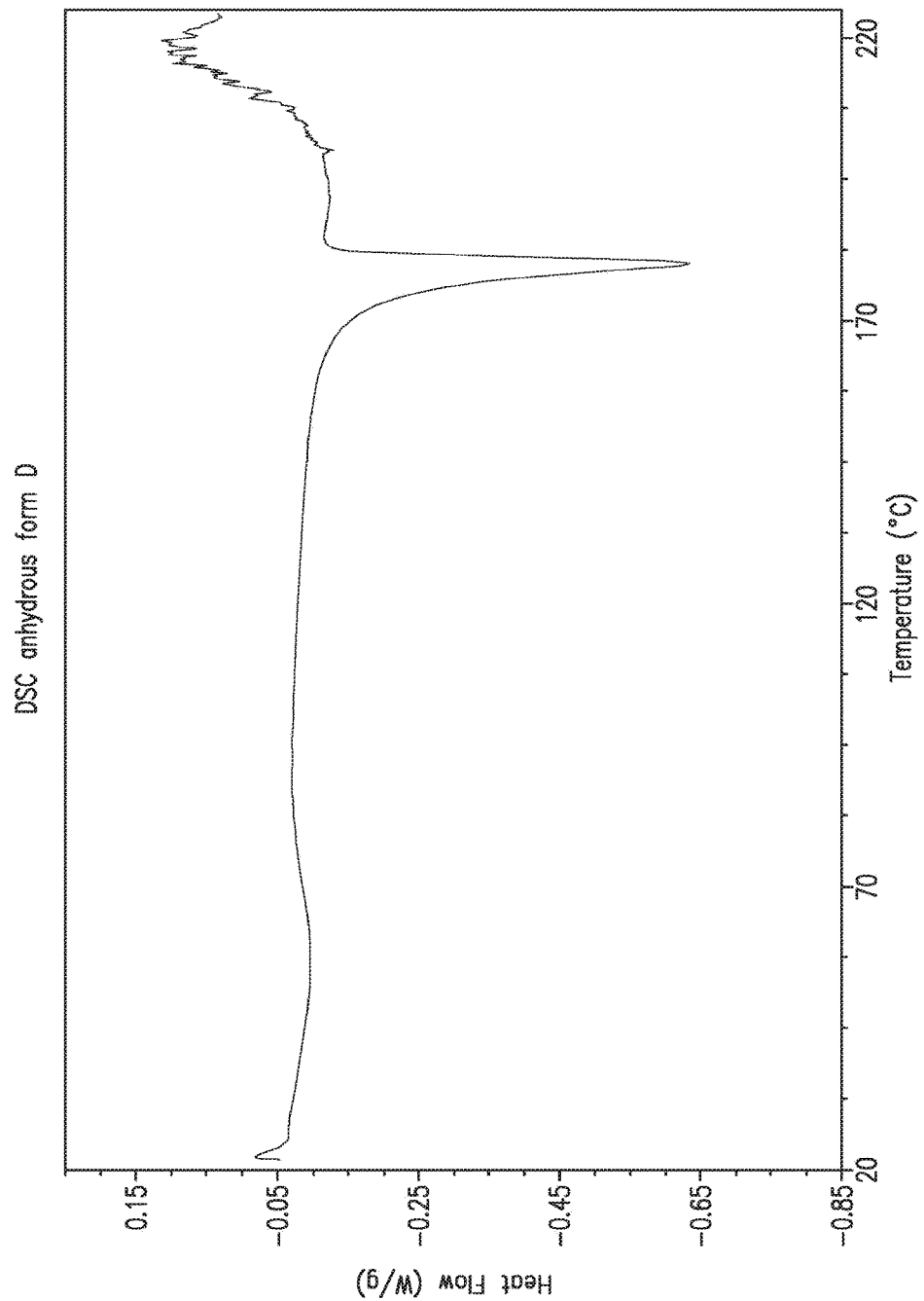
FIG. 1 depicts a Differential Scanning calorimetry (DSC) analysis for anhydrous form D.
Figure 2:
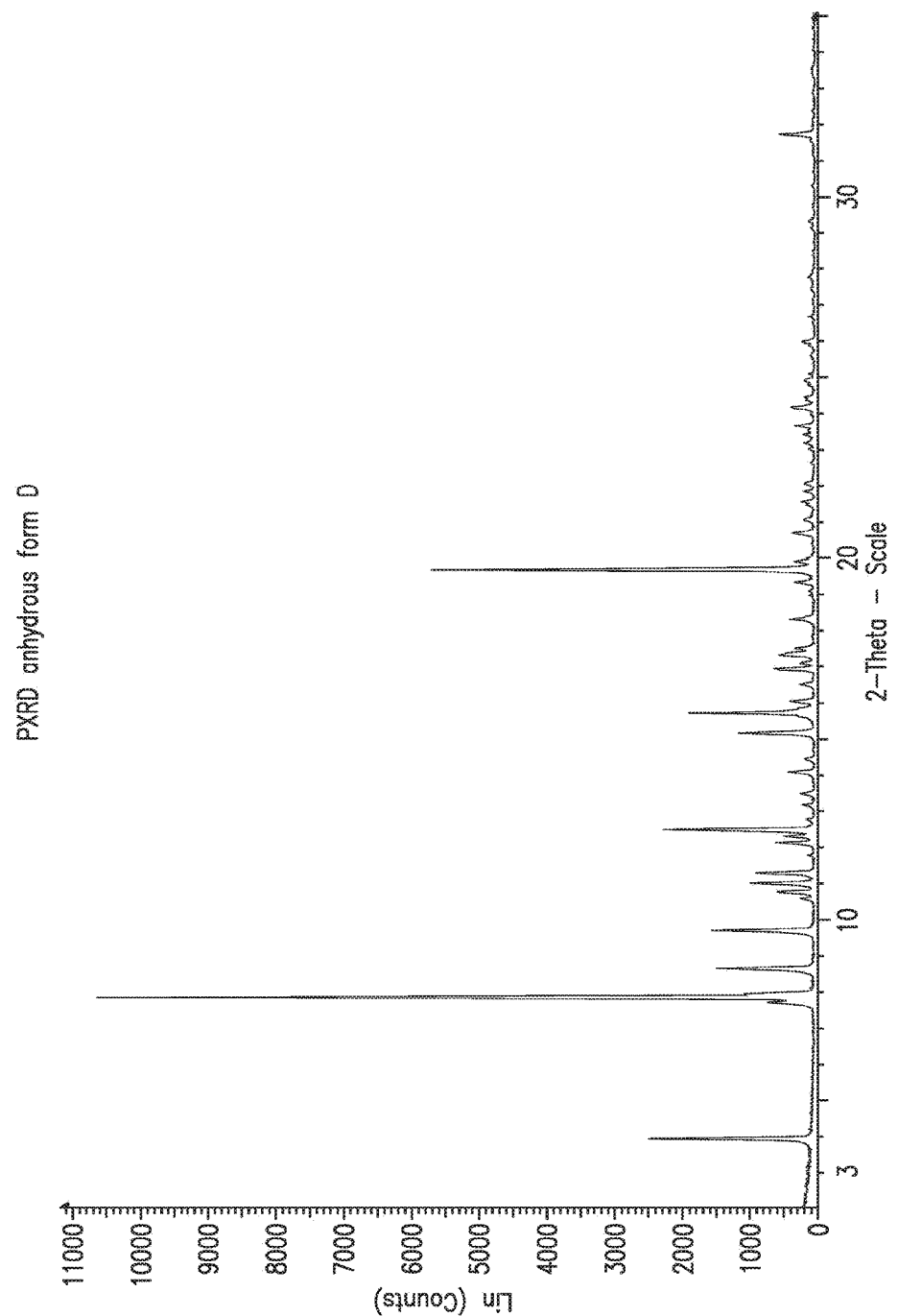
FIG. 2 depicts a Powder X-Ray Diffraction (PXRD) analysis for anhydrous form D.
Figure 3:
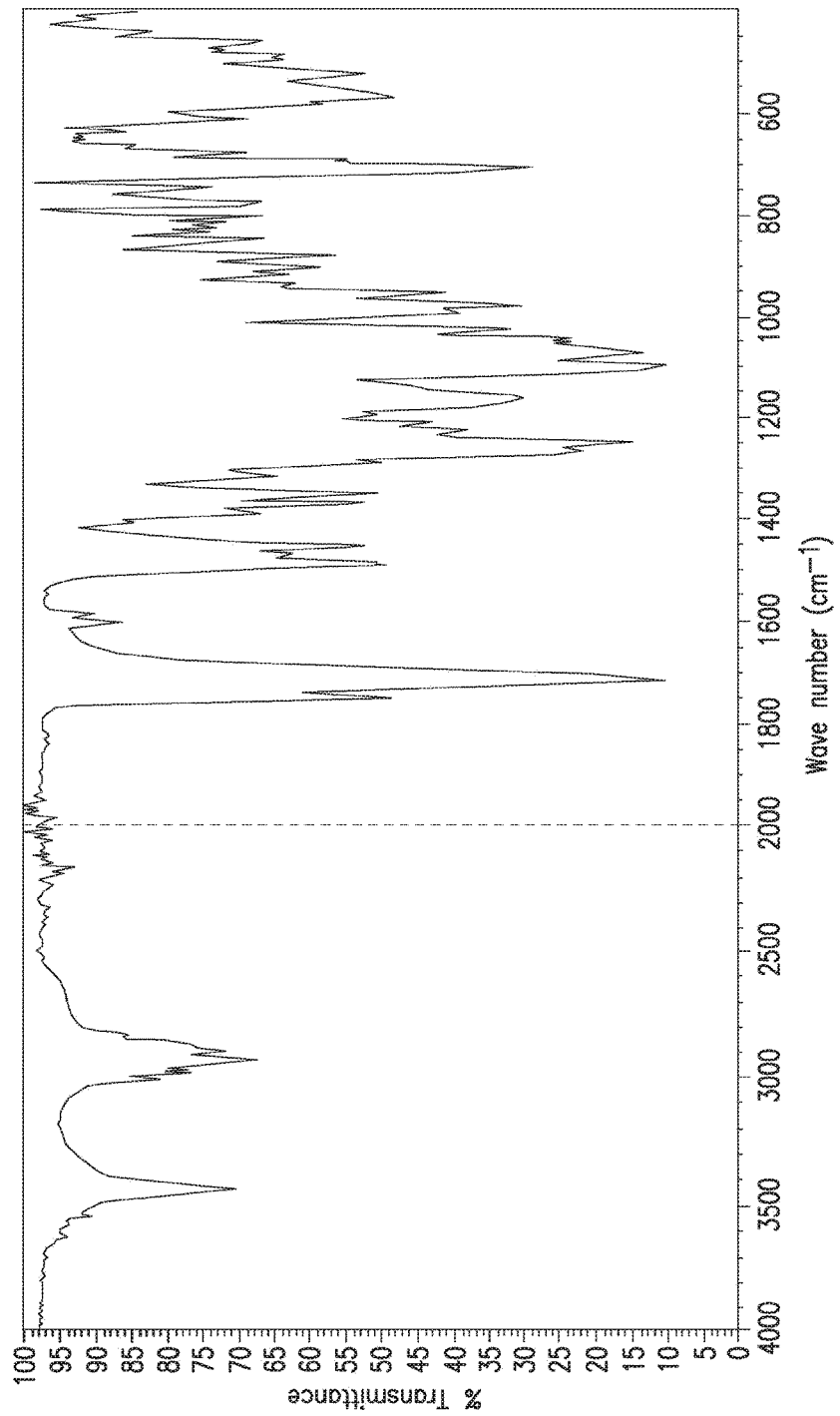
FIG. 3 depicts Fourier Transform InfraRed (FTIR) spectrometry analysis for anhydrous form D.

The anhydrous form D is obtained according to a first method by crystallization of the form A in an oil (especially Miglyol), following by rinsing with an alkane, for example heptane; the second preparation method consists in leaving a solution of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate in a mixture of Polysorbate 80, pH 3.5, ethanol and water (preferably a 25/25/50 mixture) to crystallize for approximately 48 hours. Its boiling point by DSC is approximately 175° C. (cf. FIG. 1) and is found to be the highest of all the anhydrous forms isolated. The PXRD diagram of the anhydrous form D (cf. FIG. 2) exhibits characteristic lines located at 3.9, 7.7, 7.8, 7.9, 8.6, 9.7, 10.6, 10.8, 11.1 and 12.3±0.2 degrees 2-theta. The FTIR spectrum of the anhydrous form D exhibits characteristic bands located at 979, 1072, 1096, 1249, 1488, 1716, 1747, 3436±1 cm$^{-1}$ (cf. FIG. 3). Among all the forms described in the present invention, it is the most stable anhydrous form.

The anhydrous form E is obtained at ambient temperature by maturation of the acetone form or form A in ethanol so as to intermediately form an ethanolic form which is subsequently desolvated under nitrogen sweeping or by heating at approximately 100° C. for 2 hours. Its melting point by DSC is approximately 157° C. The PXRD diagram of the anhydrous form E exhibits characteristic lines located at 7.1, 8.1, 8.9, 10.2, 10.8, 12.5, 12.7, 13.2, 13.4 and 13.9±0.2 degrees 2-theta.

The anhydrous form F is obtained by desolvating the ethanol/water heterosolvate at 120° C. under a nitrogen atmosphere for 24 hours and then maintaining in a dry environment at 0% RH at ambient temperature. Its melting point by DSC is approximately 148° C. The PXRD diagram of the anhydrous form F exhibits characteristic lines located at 4.4, 7.2, 8.2, 8.8, 9.6, 10.2, 10.9, 11.2, 12.1 and 12.3±0.2 degrees 2-theta.

There are four crystalline forms identified in ethanolic solvate or heterosolvate form:

The ethanolate form B is obtained at ambient temperature by maintaining the anhydrous form B in an ethanol-vapour-saturated environment. The PXRD diagram of the ethanolate form B exhibits characteristic lines located at 7.3, 7.8, 8.8, 10.2, 12.6, 12.9, 13.4, 14.2, 14.7 and 15.1±0.2 degrees 2-theta.

Figure 4:
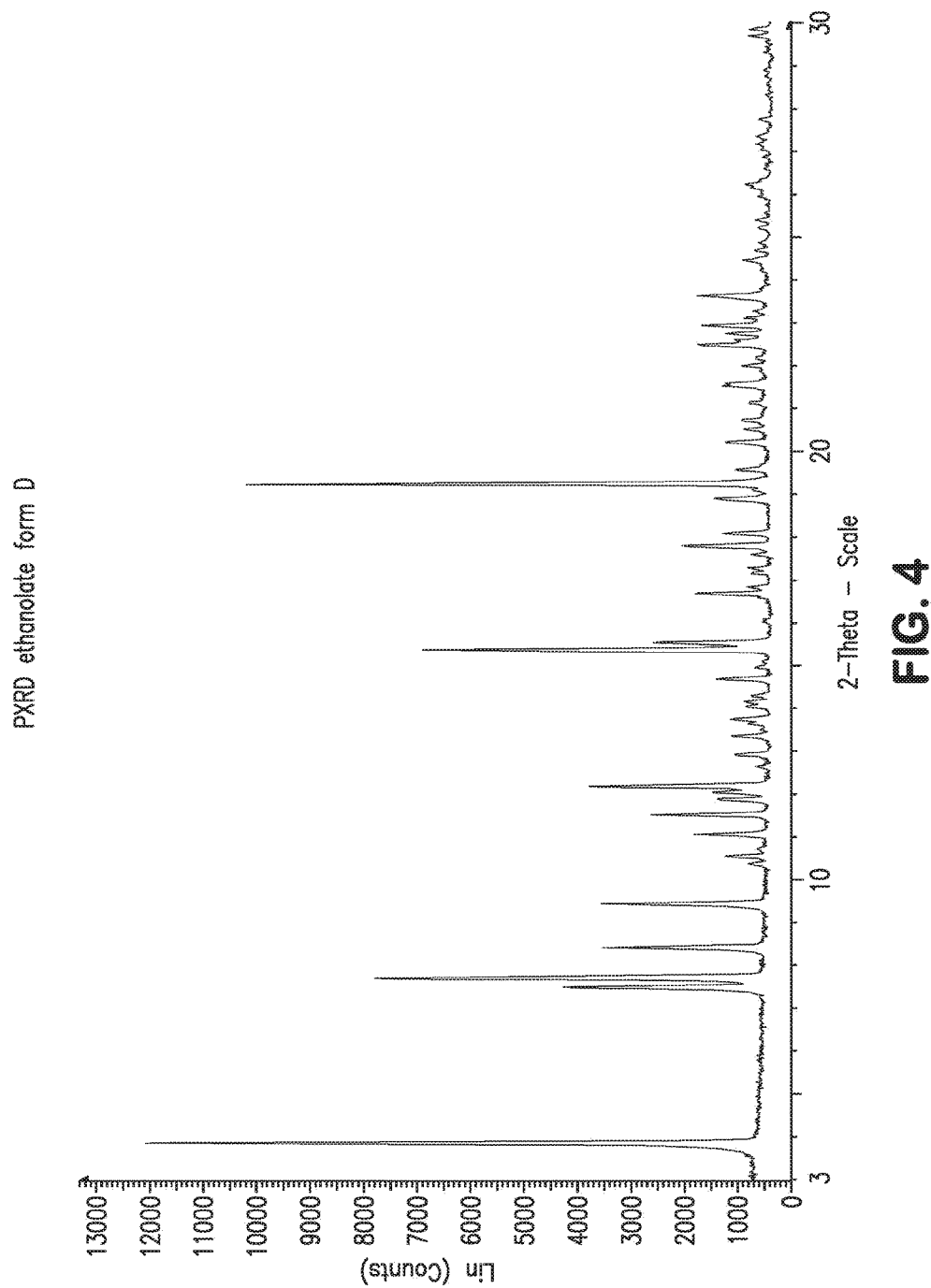
FIG. 4 depicts a Powder X-Ray Diffraction (PXRD) analysis for ethanolate form D.

The ethanolate form D is obtained at ambient temperature by maintaining the anhydrous form D in an ethanol-vapour-saturated environment. The PXRD diagram of the ethanolate form D (cf. FIG. 4) exhibits characteristic lines located at 3.8, 7.5, 7.7, 8.4, 9.4, 10.3, 10.5, 11.1, 11.5 and 11.9±0.2 degrees 2-theta.

Figure 5:
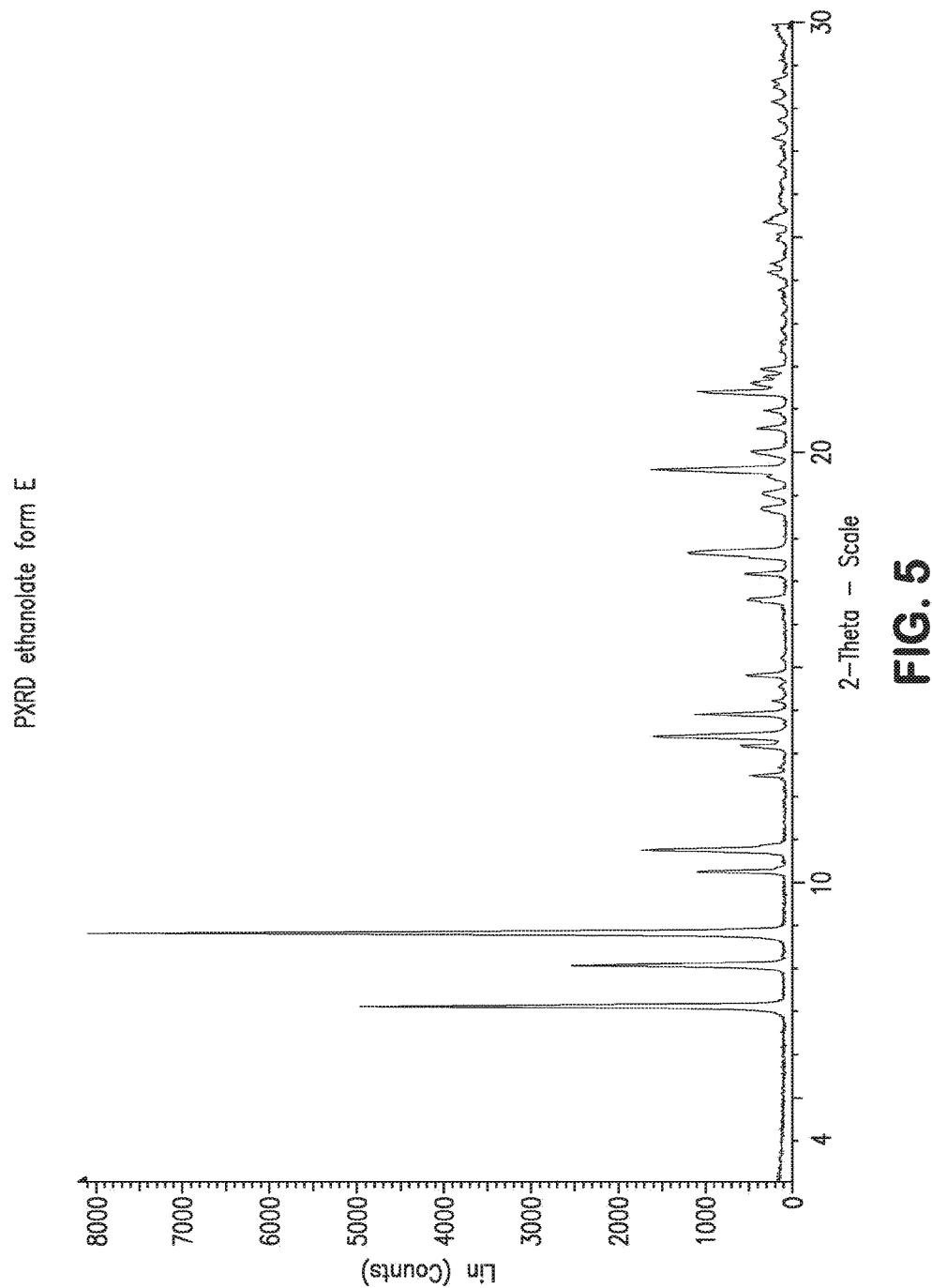
FIG. 5 depicts a Powder X-Ray Diffraction (PXRD) analysis for ethanolate form E.

The ethanolate form E is obtained at ambient temperature by maturation of the acetonate form A in ethanol. The PXRD diagram of the ethanolate form E (cf. FIG. 5) exhibits characteristic lines located at 7.1, 8.1, 8.8, 10.2, 10.7, 12.5, 13.2, 13.4, 13.9 and 14.2±0.2 degrees 2-theta.

The ethanol/water heterosolvate form F is obtained by maintaining the form B in a minimum amount of ethanol at reflux, slow cooling and isolation at ambient temperature and ambient relative humidity. The PXRD diagram of the ethanol/water heterosolvate form F exhibits characteristic lines located at 4.4, 7.2, 8.2, 8.3, 8.8, 9.6, 10.3, 10.9, 11.2 and 12.2±0.2 degrees 2-theta.

There are two crystalline forms identified in hydrate form:

The monohydrated forms C are obtained at ambient temperature by maintaining the anhydrous form C in an atmosphere containing at least 10% relative humidity. The PXRD diagram of the monohydrate form C exhibits characteristic lines located at 4.3, 6.8, 7.4, 8.6, 10.1, 11.1, 11.9, 12.2, 12.6 and 13.3±0.2 degrees 2-theta.

The dihydrate form C is obtained at ambient temperature by maintaining the anhydrous form C in an atmosphere containing at least 60% relative humidity. The PXRD diagram of the dihydrate form C exhibits characteristic lines located at 4.2, 6.9, 7.5, 8.4, 9.9, 10.9, 11.7, 12.3, 12.6 and 13.2±0.2 degrees 2-theta.

Other, nonethanolic, solvates of the form B were prepared, such as in particular those obtained with the following solvents: dichloromethane, diisopropyl ether, n-propanol, isopropanol, toluene, methyl isobutyl ketone, tetrahydrofuran, dimethylformamide, ethyl acetate, etc.

The present invention will be described more fully by means of the following examples which should not be considered to limit the invention.

Experimental analysis conditions:

Differential Scanning Calorimetry (DSC):

The measurements were carried out on a T.A. Instruments DSC2010 thermal analyser. The sample is subjected to temperature programming from 25° C. to 225° C. with a heating rate of 5° C/min. The product is placed in a crimped aluminium capsule and the amount of product analysed is between 2 and 5 mg. Constant nitrogen sweeping at 55 mL/min is used in the oven chamber.

Powder X-Ray Diffraction (PXRD):

The analyses were carried out on a Panalytical X'Pert Pro diffractometer with a reflection-mode Bragg-Brentano focusing geometry (θ-2θ) assembly. The product analysed is deposited as a thin layer on a silicon single crystal. A copper anticathode tube (45 kV/40 mA) supplies an incident radiation Cu K$\alpha_1$ (λ=1.5406 Å). The beam is collimated using Sollers slits which improve the parallelism and variable slits which limit scattering. An X'Celerator detector completes the device. The diagram recording characteristics are the following: sweeping from 2 to 30 degrees 2θ, counting time from 100 to 500 seconds per step with a step of 0.017°.

Fourier Transform InfraRed (FTIR) spectrometry:

The solid samples were analysed using a Nicolet Nexus spectrometer. The analysis is carried out by attenuated total reflectance (ATR) using a Smart Orbit accessory from the company Thermo (single reflection diamond crystal ATR accessory). The spectral range swept is between 4000 and 400 $cm^{-1}$ with a resolution of 2 $cm^{-1}$ and an accumulated scan number of 20.

EXAMPLE 1

Two tests of dissolution of approximately 550 mg of 4-acetoxy-2α-benzoyloxy-5β,20-epoxy-1-hydroxy-7β,10β-dimethoxy-9-oxotax-11-en-13α-yl (2R,3S)-3-tert-butoxy-carbonylamino-2-hydroxy-3-phenylpropionate in 14 g of Miglyol 812 Neutral oil, Sasol are carried out. Magnetic stirring is carried out at 500 rpm for 24 hours at ambient temperature.

After one week, the samples are vacuum-filtered and rinsed with heptane. Each sample is analysed by PXRD for confirmation of the form obtained. After filtration, between 300 and 350 mg of anhydrous form D are obtained.

EXAMPLE 2

Approximately 3 g of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenyl-propionate are dissolved in a mixture of 50 mL ethanol+50 mL Polysorbate 80, pH 3.5. 100 mL of water are added to the previous mixture and the whole is homogenized. After storage for 48 hours at ambient temperature, crystals of anhydrous form D appeared. The amount of crystallized product recovered by filtration is approximately 2.45 g.

A comparative stability study was carried out between the acetone solvate form A and the anhydrous form D. The comparison of the PXRD analyses carried out on the A and D forms immediately after production and after having maintained said forms at 40° C. for one month gives the following results:

Form A: partial desolvation resulting in a mixture of the acetone solvate form A and of the anhydrous form B being obtained.

Form D: no change detected after maintaining at 40° C. for one month.

What is claimed is:

1. Anhydrous form F of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenyl-propionate, characterized by a PXRD diagram exhibiting characteristic lines located at 4.4, 7.2, 8.2, 8.8, 9.6, 10.2, 10.9, 11.2, 12.1 and 12.3±0.2 degrees 2-theta.

* * * * *